United States Patent [19]

Kuzara

[11] Patent Number: 4,711,244

[45] Date of Patent: Dec. 8, 1987

[54] DIGITAL MOISTURE DERMATOMETER

[75] Inventor: David J. Kuzara, New City, N.Y.

[73] Assignee: American Cyanamid Company, Stamford, Conn.

[21] Appl. No.: 775,939

[22] Filed: Sep. 12, 1985

Related U.S. Application Data

[63] Continuation of Ser. No. 331,729, Dec. 17, 1981, abandoned.

[51] Int. Cl.⁴ .............................................. A61B 5/00
[52] U.S. Cl. .................................. 128/632; 324/61 P; 73/73
[58] Field of Search ............. 128/632, 734; 324/61 R, 324/61 P, 61 QS; 73/73, 74, 336.5; 361/286

[56] References Cited

U.S. PATENT DOCUMENTS 3,761,810 9/1973 Fathauer .......................... 324/61 R
4,013,065 3/1977 Copeland et al. .................... 128/632
4,114,090 9/1978 Paskitt ............................. 324/61 QS
4,199,984 4/1980 Huddart et al. ............... 324/61 R X

FOREIGN PATENT DOCUMENTS 2919230 11/1980 Fed. Rep. of Germany ... 324/61 QS Primary Examiner—Lee S. Cohen
Attorney, Agent, or Firm—C. J. Fickey

[57] ABSTRACT

An improvement in a device to measure the moisture content of the *stratum corneum* of human skin by means of a stray field capacitance transducer, the measurement of the stray field being accomplished by using an oscillating electronic circuit, in which said stray field capacitance being measured is a frequency determining element of the circuit, and a signal proportional to the period of oscillation of the circuit is a measurement of the relative moisture content of the outer layer of the object being measured.

5 Claims, 5 Drawing Figures

PROBE MECHANICAL COMPONENTS

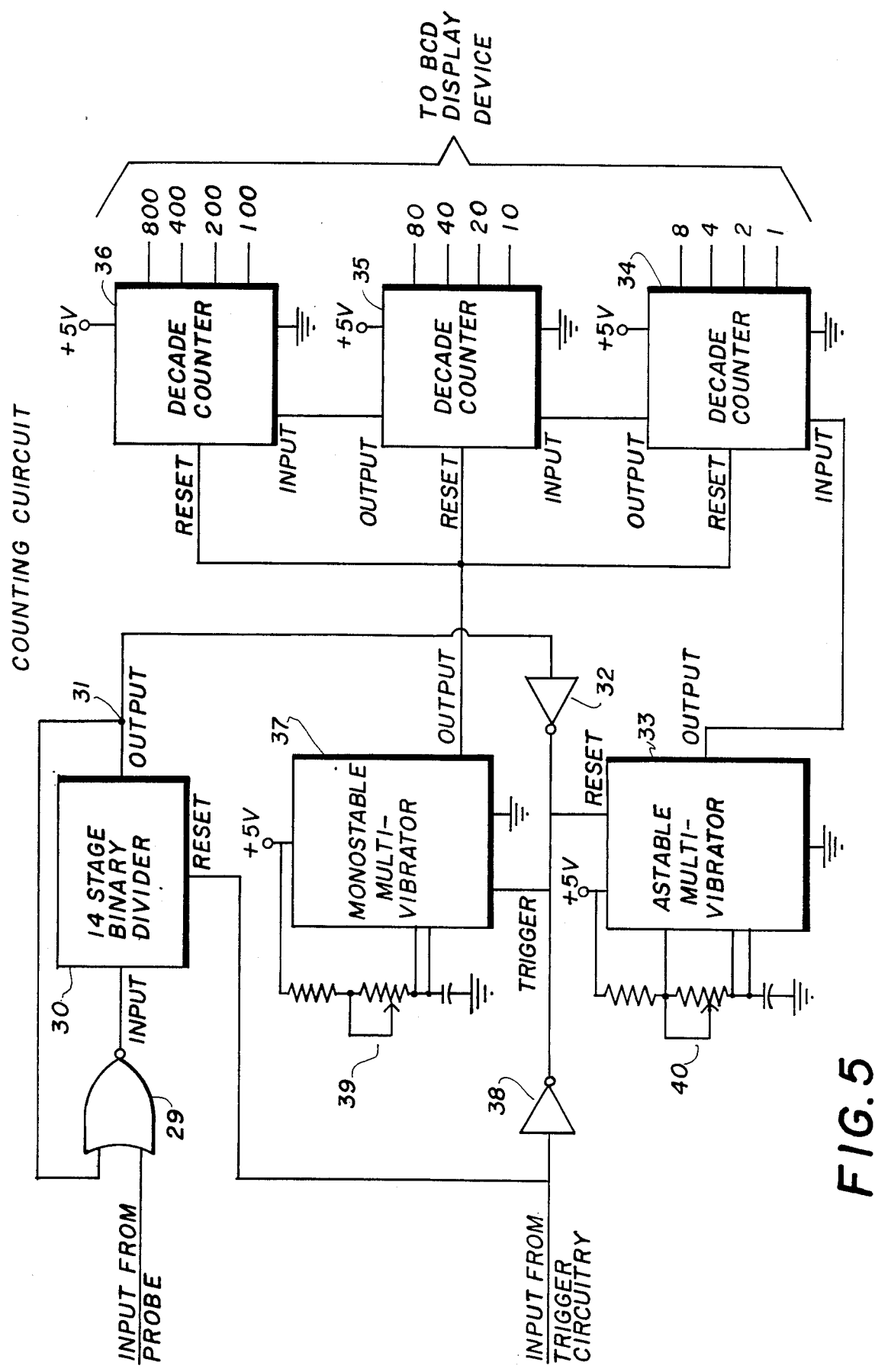

DIGITAL MOISTURE DERMATOMETER

This application is a continuation of application Ser. No. 331,729, filed Dec. 17, 1981, now abandoned.

BACKGROUND OF THE INVENTION

This invention relates to an improvement in a device used to measure moisture in a substrate. More particularly the invention resides in an improvement to a moisture dermatometer as described in U.S. Pat. No. 4,013,065.

A moisture dermatometer is a device for measuring the moisture content of human skin (the *statrum corneum*). For cosmetic or other purposes, it is desirable to be able to determine the moisture in the skin. The measurement of the moisture content of the *stratum corneum* requires an instrument which is sensitive over a small range of skin depth. The *stratum corneum* is surrounded on one side by the outside environment with relatively low moisture content, and on the other side by the deeper layers of the skin with much higher moisture content.

The ideal instrument should sense moisture only in this narrow region. The moisture dermatometer of U.S. Pat. No. 4,013,065 uses a stray field capacitor to sense changes in the dielectric constant of the outer layer of the skin which is directly influenced by its moisture content, said device also incorporates an A.C. voltage divider technique whereby changes in the capacitance of the stray field capacitor are reflected as amplitude modulation of a carrier waveform. However, several deficiencies are evident when this technique is employed, for example: (a) the amplitude modulation sensitivity to noise reduces the reproducability of the readings; (b) the output signal being inversely proportional to moisture content, thus requiring that the output signal be processed further to provide a reading that would directly reflect an increase in moisture content; and (c) the inability to obtain a reading at a predetermined time interval after contact with the skin.

The instant invention provides an improvement means to overcome each of the aforesaid shortcomings.

SUMMARY OF THE INVENTION

The present invention, which resides in an improvement to U.S. Pat. No. 4,013,065, also uses a stray field capacitive sensor to measure the moisture content of the *stratum corneum* of the human skin. However, a frequency modulation technique was substituted in place of the amplitude modulation technique employed in the prior art. This change was employed to reduce noise pickup. In addition, each reading was determined from 8,192 separate measurements which increased the signal to noise ratio by a factor of the $\sqrt{8,192}$ or 90. Thus, the final reading is linearly proportional to the stray field capacitance and, therefore, proportional to moisture content without need for further processing. Finally, this invention provides a sensory means linked to the contact of the stray field capacitor with the skin that affords a means to take a reading at a predetermined period after skin contact.

DESCRIPTION OF THE DRAWINGS

The invention may be better understood by reference to the drawings in which:

FIG. 5 Is a diagram of the circuitry for processing the electrical signal from the probe.

DETAILED DESCRIPTION OF THE PREFERRED EMBODIMENT

Figure 1:
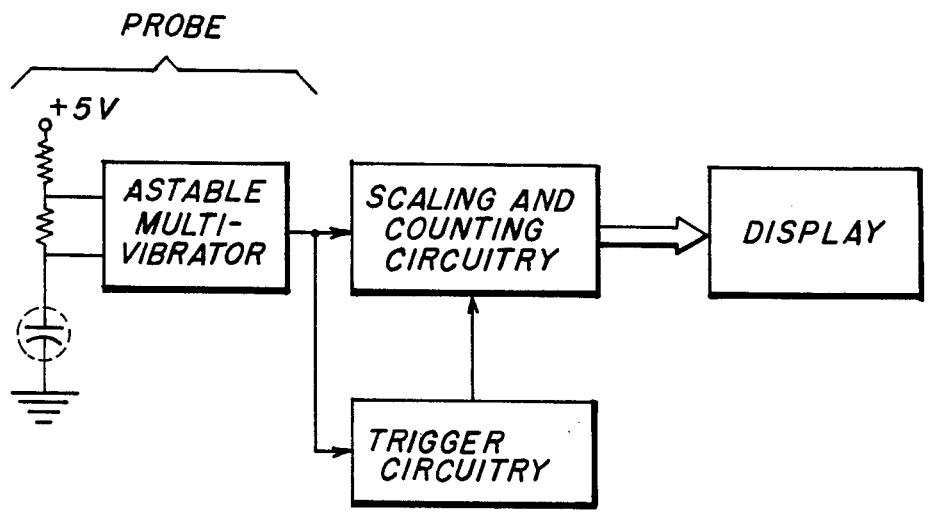
FIG. 1 is a block diagram of the components of the digital moisture dermatometer.

With reference to FIG. 1, the probe signal is generated by an astable multivibrator whose frequency-determining elements are two fixed resistors and the stray field capacitor. The output of the astable multivibrator is a square wave whose period is proportional to the capacitance of the stray field capacitor. Introduction of a dielectric material into the stray field region of the capacitor increases its capacitance and causes a proportional increase in the period of the output signal. The astable multivibrator circuity is contained within the probe to avoid noise pickup. The output signal is fed via a shielded cable and a connector into an instrument cabinet, not shown.

The instrument cabinet contains: scaling and counting circuitry to process the output signal, a triggering circuit to initiate the processing, a digital display, controls for zeroing and calibrating the instrument, a switch for selecting the method of triggering, a regulated power supply, and a power switch.

The probe incorporates a spring-loaded mechanism to insure a constant contact force when measuring.

Figure 2:
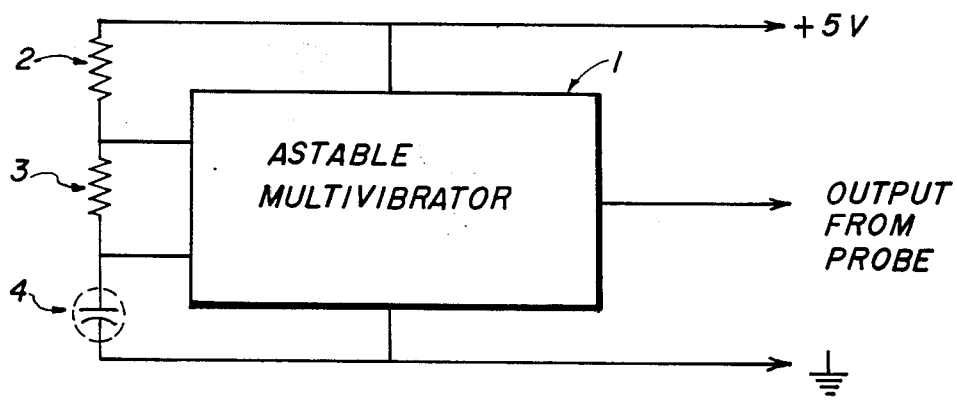
FIG. 2 is a detailed circuit diagram of the probe.

Referring to FIG. 2, showing the probe circuitry in greater detail, the probe contains an astable multivibrator integrated circuit 1 which produces a square wave output of variable frequency. Resistors 2 and 3 are part of the frequency-determining circuitry of the astable multivibrator. The stray field capacitor 4 is located on the probe face and is also part of the frequency-determining circuitry of the astable multivibrator. When the probe is pressed onto a dielectric material, the capacitance of the stray field capacitor 4 is increased and the period of the output waveform is proportionally increased.

The probe operates off a regulated positive voltage which is supplied from the instrument cabinet via a connector and a shielded cable. The probe output passes through the same cable to the instrument cabinet.

Figure 3:
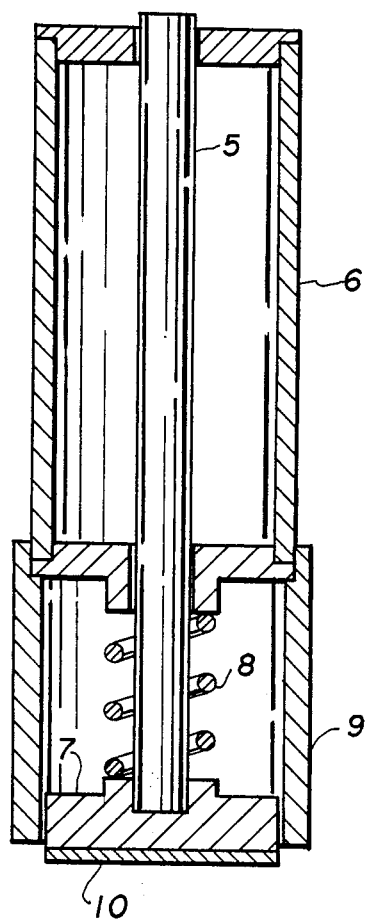
FIG. 3 is a diagramatic illustration of the mechanical features of the dermatometer probe.

Also incorporated within the probe is a mechanism to enhance the accuracy of the measurement by ensuring that the stray field capacitor disk is applied to the substrate under test with a constant force. (See FIG. 3). An inner shaft 5 slides within an outer housing 6. The mount 7 that holds the stray field capacitor disk 10 is mounted on the inner shaft 5 and its motion is retarded by the compression of spring 8. Outer sleeve 9 serves as a stop to halt the sliding of mount 7 at a fixed distance. Since spring 8 is held at a fixed compression, it forces stray field capacitor disk 10 against the substrate at a fixed pressure.

Figure 4:
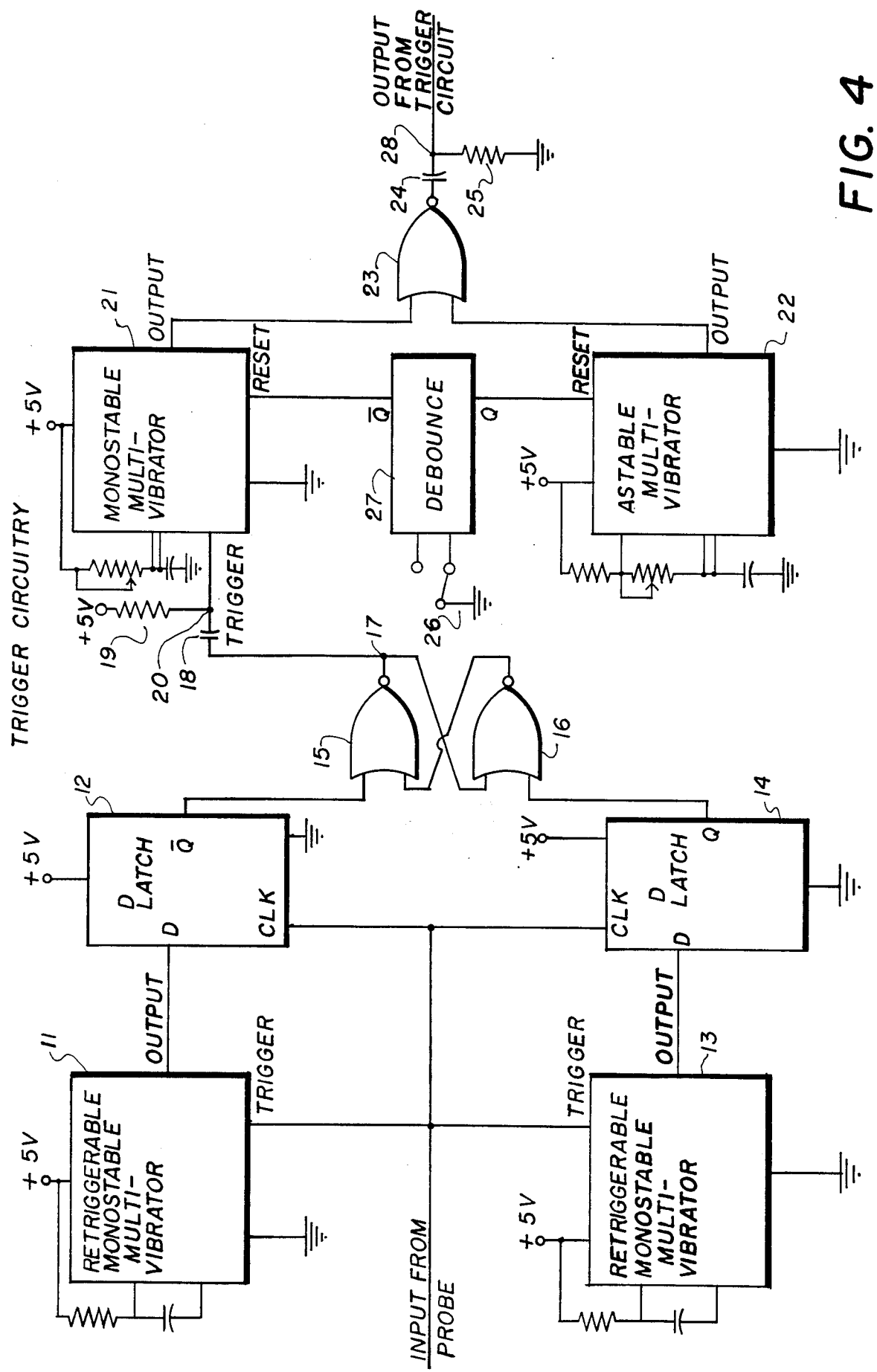
FIG. 4 is a diagram of the circuitry for producing a trigger signal to initiate the taking of a reading.

The output signal from the probe goes to the trigger circuitry and to the scaling and counting circuitry. In the trigger circuitry (see FIG. 4), the up transitions of the probe output square wave are used to trigger two retriggerable monostable multivibrators and two D-latches 12 and 14. The output of monostable multivibrator 11 goes to the D input of D-latch 12, and the output of monostable multivibrator 13 goes to the D input of D-latch 14. Each of the two multivibrator-D-latch combinations acts as a period comparator. If the period of the input signal is smaller than the pulse width of the monostable multivibrator, the output of the corresponding D-latch will be high. If the input period is larger than the pulse width of the monostable multivibrator, the D-latch output will be low. The pulse width of monostable multivibrator 11 is set to be slightly larger than the pulse width of monostable multivibrator 13. The $\overline{Q}$ output of D-latch 12 goes to one input of nor-gate 15, while the Q output of D-latch 14 goes to one input or nor-gate 16. Nor-gates 15 and 16 are cross coupled to make a period comparator with hysteresis. The voltage at point 17 will go low only when the period of the input signal rises above the pulse width of monostable multivibrator 11 and it will go high only when the input signal period falls below the pulse width of monostable multivibrator 13. Capacitor 18 and resistor 19 A.C. couple the voltage at point 17 such that the voltage at point 20 is normally high but falls momentarily low when the voltage at point 17 falls low. This low pulse triggers monostable multivibrator 21. Thus monostable multivibrator 21 is triggered only when the period of the probe input signal rises above the pulse width of monostable multivibrator 11. Using a period comparator with hysteresis gives the circuit more immunity from noise and prevents spurious triggerings.

The outputs of monostable multivibrator 21 and astable multivibrator 22 go to inputs of nor-gate 23. The output of nor-gate 23 is A.C. coupled by capacitor 24 and resistor 25 to provide a momentary high pulse whenever the output of nor-gate 23 goes high. The output of switch 26 is connected, through debouncing circuitry 27 of the reset inputs of monostable multivibrator 21 and astable multivibrator 22 such that only one of these two circuit elements can be enabled at any one time.

When switch 26 is in the first position astable multivibrator 22 is disabled and monostable multivibrator 21 is enabled. Thus, when the period of the input signal from the probe rises above the pulse width of monostable multivibrator 11, monostable multivibrator 21 is triggered and this generates a trigger pulse at point 28 at the end of its timing cycle. In actual practice, the pulse width of monostable multivibrator 13 is set just above the normal period of the probe input signal for the probe in air, and the pulse width of monostable multivibrator 11 is set slightly higher still. Thus, when the probe is placed on a surface of appreciable dielectric constant, the period of the input signal rises, and a trigger signal is generated at point 28 after a delay of one pulse width of monostable multivibrator 21. This delay insures that all contact transients have passed and that the correct contact pressure has been achieved before a reading is taken.

When switch 26 is in the second position, monostable multivibrator 21 is disabled and astable multivibrator 22 is enabled. Thus astable multivibrator 22 continuously generates trigger pulses at point 28, regardless of the environment of the probe disc. This produces continuous readings and is useful when calibrating the instrument.

With reference to FIG. 5, the output from the probe is fed to one input of nor-gate 29. The output of nor-gate 29 goes to the input of 14 stage binary divider 30 and the output of binary divider 30 [point 31] goes to the other input of nor-gate 29. If the signal at point 31 is high, it will hold the output of nor-gate 29 low, and thus prevent the binary divider from incrementing. When a momentary reset pulse is applied, the count of binary divider 30 is reset to zero and the signal at point 31 goes low. This allows the input signal from the probe to propagate past nor-gate 29 and increment binary divider 30. After 8192 periods of the input signal, the signal at point 31 again goes high, disabling the binary divider until another reset signal occurs. The advantage of this arrangement is twofold: (1) it allows astable multivibrator 1, in the probe, to operate at a high frequency. This reduces the error in the period due to noise; (2) it effectively averages 8192 periods so that the effect of any random errors in the period is greatly reduced.

The signal at point 31 passes through inverter gate 32 and goes to the reset input of astable multivibrator 33. Thus, when the signal at point 31 is high, astable multivibrator 33 is disabled and its output is low. When the signal at point 31 is low, astable multivibrator 33 is enabled and it outputs a square wave. The output of astable multivibrator 33 goes to the input of decade counter 34. Decade counters 34, 35 and 36 are connected together to form a three digit counter with a binary coded decimal (BCD) output for each digit. These BCD outputs are connected to a display device to display a number which is the value of the reading.

The output of monostable multivibrator 37 is connected to the reset inputs of decade counters 34, 35 and 36. Thus, when monostable multivibrator 37 is triggered, its output goes high, resetting counters 34, 35 and 36 to zero. This also prevents the counters from counting any pulses until the output of monostable multivibrator 37 goes low again.

The trigger pulse from the trigger circuitry goes to the reset input of binary divider 30 and, through inverter 38 to the trigger input of monostable multivibrator 37. When a trigger pulse occurs, it triggers monostable multivibrator 37, which holds the counter output at zero for one timing cycle. The trigger pulse also starts the timing cycle of binary divider 30, which enables astable multivibrator 33 for a period of time proportional to the period of the input signal from the probe. The pulse width of monostable multivibrator 37 is changed via potentiometer 39 to offset the reading. The frequency of astable multivibrator 33 is changed via potentiometer 40 to scale the reading. To calibrate, the probe is placed in air and potentiometer 39 adjusted until the reading is zero. Then the probe is placed in distilled water and potentiometer 40 is adjusted until the reading is one hundred.

I claim:

1. An improved instrument of the type for making random, on demand measurements on the stratum corneum of the skin, said instrument having a stray field capacitance transducer for making said measurements, the improvement which comprises
    (a) an oscillator circuit, comprising an oscillator of predetermined frequency and said stray field capacitance transducer, whereby said oscillator frequency varies in accordance with the capacitance measurement of said transducer,
    (b) a readout means adapted to receive and display said oscillator frequency, and
    (c) a trigger means coupled to said oscillator circuit and said readout means for obtaining a reading on said readout means, said trigger means comprising means to provide a fixed frequency, means to compare said fixed frequency to said oscillator frequency, and means to enable said readout means when said oscillator frequency exceeds said fixed frequency.

2. The invention according to claim 1, wherein said readout means comprises:
(a) counter means;
(b) means to produce a train of pulses at a uniform time interval; and
(c) means to enable said counter means to count said pulses for a predeterminable number of oscillations of said oscillator circuit.

3. The invention according to claim 2, said readout means further comprising:
(a) a time delay circuit;
(b) a means operatively connected to said time delay circuit and responsive to said stray field capacitance transducer for contacting said stratum corneum for initiating said time delay circuit; and
(c) a means operatively connected to said time delay circuit for initiating said readout means after a predetermined time.

4. An improved instrument of the type having a stray field capacitance transducer means for measuring, and a readout means operatively associated with said stray field capacitance transducer means, for displaying the moisture content of human skin, wherein the improvement comprises:
(a) a measurement enabling circuit operatively associated with said readout means;
(b) oscillator circuit means connected to said measurement enabling circuit and said stray field capacitance transducer means, said oscillator circuit means being responsive to said stray field capacitance transducer means being brought in contact with said human skin and thereby initiating said measurement enabling circuit, wherein said oscillator circuit means comprises a square-wave oscillator circuit, the period of the output from said oscillator circuit means being in direct proportion to the capacitance of said stray field capacitance transducer means.

5. The invention according to claim 4, wherein said measurement enabling circuit comprises:
(a) a first monostable multivibrator means for producing an output having a pulse duration longer than the period of the output of said square-wave oscillator circuit when said stray field capacitance transducer means is not in contact with said human skin;
(b) a second monostable multivibrator means for producing an output having a pulse duration longer than the pulse duration of said first monostable multivibrator means; and
(c) comparison circuit means that enables said readout means when the period of the output of said squarewave oscillator circuit changes from a value less than the pulse duration of said first monostable multivibrator means to a value greater than the pulse duration of said second monostable multivibrator means.

* * * * *